United States Patent [19]

Reif

[11] Patent Number: 4,607,228

[45] Date of Patent: Aug. 19, 1986

[54] APPARATUS AND METHOD FOR MEASURING THE CONCENTRATION OF SOLID PARTICLES IN A FLUID STREAM

[75] Inventor: Robert B. Reif, Grove City, Ohio

[73] Assignee: Battelle Development Corporation, Columbus, Ohio

[21] Appl. No.: 570,300

[22] Filed: Jan. 13, 1984

[51] Int. Cl.[4] ............................................. G01N 27/60
[52] U.S. Cl. ........................................ 324/454; 73/28; 324/453
[58] Field of Search ............... 324/453, 454, 464, 452, 324/71.4; 73/28, 432 PS; 55/103, 105, 146, 270

[56] References Cited

U.S. PATENT DOCUMENTS

| | | | |
|---|---|---|---|
| 2,434,835 | 1/1948 | Colley | 324/71.4 |
| 2,758,666 | 8/1956 | Prentiss | 55/103 |
| 3,784,902 | 1/1974 | Huber | 324/71.4 |
| 4,063,153 | 12/1977 | Dechene et al. | 324/30 R |
| 4,074,184 | 2/1978 | Dechene et al. | 324/30 R |
| 4,082,994 | 4/1978 | Newton | 324/30 R |
| 4,288,741 | 9/1981 | Dechene et al. | 324/61 R |
| 4,291,273 | 9/1981 | Dechene et al. | 324/343 |
| 4,309,661 | 1/1982 | Kamoto | 324/453 |
| 4,531,402 | 7/1985 | Reif et al. | 73/28 |

Primary Examiner—Stewart J. Levy
Assistant Examiner—Kevin D. O'Shea
Attorney, Agent, or Firm—Sidney W. Millard

[57] ABSTRACT

Apparatus for measuring the concentration of solid particles in a fluid stream wherein a critical flow orifice produces a stream of fluid having a constant velocity, a surface for effecting triboelectric charging of the particles in the gas in the constant velocity stream and a charge measuring device for measuring the charges thus triboelectrically imparted to the particles. The apparatus overcomes the inaccuracies which occur in prior art particle detectors when such particle detectors are used to monitor fluid streams whose velocity is variable e.g. air intake systems for internal combustion engines which operate at varying speeds.

22 Claims, 4 Drawing Figures

APPARATUS AND METHOD FOR MEASURING THE CONCENTRATION OF SOLID PARTICLES IN A FLUID STREAM

BACKGROUND OF THE INVENTION

This invention relates to an apparatus and method for measuring the concentration of solid particles in a fluid stream. More particularly, the invention relates to an apparatus and method in which measurement of the concentration of solid particles is effected by triboelectrically charging the particles in part of the stream and then measuring the charges upon the particles.

It is known to measure the concentration of solid particles in a gas by drawing a sample of the gas over an electrode. The impacts of particles in the gas sample upon the electrode cause frictional or triboelectric charging of the particles and the electrode and the resultant charge upon the electrode can be detected by appropriate circuitry, thereby giving a measurement of the concentration of particles in the gas. In one known form of such a device intended for use in sampling air within a building or plant, the electrode projects into the center of a venturi tube. Downstream from the electrode, motive air inlet tubes intersect the venturi. Air under pressure is fed into the motive air inlet tubes, thereby drawing air through the venturi tube over the electrode and permitting the electrode to measure the concentration of dust particles in the air sample.

It appears that this type of dust measuring device can give acceptable results when the air to be sampled is essentially static, as for example in a room. However, many of the most important applications of dust detecting devices involve determining the concentration of solid particles in moving gas streams. For example, dust detection devices may be used for checking the efficiency of dust removal equipment used in certain environmental control systems (e.g. removal of fibers from the air in textile mills or removal of dust in grain elevators) and for these purposes it will be desirable to install the dust detection apparatus in the moving stream of air immediately downstream of the dust removal equipment. Similarly, particle detection equipment may be used for detecting dust, soot, solid pollutants and other particles in waste gases, such as gases in flues, automobile exhaust systems, cement kilns and power generation plants, where streams of gas may be moving with considerable velocities. In many of these cases, the velocity of the gas stream can be expected to vary with time depending upon the level at which the plant is being operated.

One particularly important application of particle detection devices where wide variations in the velocity of the gas streams involved must be expected is monitoring of the efficiency of air cleaning systems used in conjunction with internal combustion engines and similar devices. Internal combustion engines require a large supply of clean air to ensure maximum engine performance and engine life and to reduce maintenance requirements. Air cleaning systems have been developed which will remove 99% of the particulate matter which is drawn into the air intake systems. Such high efficiency air cleaning systems are multi-stage units which include barrier type air filters. However, a simple dust leak in the air cleaning system (caused by, for example, accidental perforation of one of the air filters) can negate the effectiveness of the system. The vehicle operator must know when such a leak occurs so that he can shut off the engine and take steps to correct the leak problem before irreparable damage is done. This problem is especially of concern on military tanks equipped with gas turbine engines which are highly susceptible to damage by dust in the air under some operating conditions. Also, problems with excessively dusty air may be encountered in other internal combustion engines equipped with turbo chargers. A reliable dust detection system can also be valuable on any engine and on many other systems where filters are used to remove dust from the air to provide a supply of clean air for an air-consuming device. One type of particle detection device which relies upon triboelectric charging is disclosed in U.S. patent application Ser. No. 490,533 filed May 2, 1983 by myself and Loren R. Albrechtson, now U.S. Pat. No. 4,531,402, issued July 30, 1985.

One potential advantage of particle detectors relying upon triboelectric charging for monitoring the efficiency of air filtration systems is that such triboelectric particle detectors do have some capacity for distinguishing between large and small particles in a gas stream whereas, for example, filter-type particle detectors tend to measure only the total weight of the particles per unit volume without regard to their size. The ability of triboelectric particle detectors to distinguish between large and small particles is important because many engines and other gas-consuming devices can tolerate the presence of very small particles (such as those found in many smokes) but are highly susceptible to damage by relatively large particles (typically those exceeding 5 microns in diameter). If one fits an engine or similar gas-consuming device with a particle detector for measuring the concentration of particles in the air entering the engine or other device and this particle detector does not distinguish between large and small particles, the particle detector will yield a considerable number of "false alarms" when the incoming air contains small particles which are sufficient to actuate the particle detector but which would not actually be harmful to the engine or the device. Such false alarms are obviously undesirable since they unnecessarily increase the down time of the engine or other device and may result in unnecessary maintenance costs. This problem of false alarms is exacerbated by the fact that the air filtration system of an engine or other device which is not harmed by very small particles will often, in order to present as little resistance to air flow as possible, be designed so that such very small particles pass the air filtration system and only the larger, potentially damaging particles are retained by the system. Thus, triboelectric particle detectors are potentially valuable in monitoring the performance of many air filtration systems used in practice. In addition, such triboelectric particle detectors can be made relatively simple in construction; for example, in the type of static air particle detector described above which uses motive air inlet tubes to draw a sample of air through a venturi tube, it would appear that where this type of particle detector is to be used to sample a stream of air which is already moving, the motive air inlets could be omitted, thereby producing an extremely simple type of particle detector.

Unfortunately, I have found that it is difficult to obtain consistent readings from triboelectric particle detectors which are used to measure the concentration of particles in moving streams of air which are susceptible to considerable changes in velocity, such as those experienced by the streams passing through air filtration systems of internal combustion engines (where the air stream velocity varies substantially linearly with engine speed); as already noted, particle detectors are also used in several other fields where the velocity of the gas stream being monitored can vary over a wide range. I have found that, even though the concentration of particles in the gas stream passing through a triboelectric particle detector remains constant, the apparent particle concentration indicated by the triboelectric particle detector increases with increased gas velocity. Thus, when a triboelectric particle detector is being used to monitor air being supplied from an air filtration system to an internal combustion engine, at high engine speed the triboelectric particle detector may indicate a dangerously high particle concentration, although in fact the particle concentration is within the acceptable range. Such susceptibility to false alarms at high engine speeds is particularly unfortunate since the operator is most likely to be given a false alarm when the vehicle he is driving is travelling at high speed, perhaps upon an expressway or similar highway, when it may be most inconvenient to stop the vehicle in order to check the functioning of the air filtration system.

Accordingly, there is a need for a triboelectric particle detector capable of measuring particle concentration in moving streams of fluid which is not greatly affected by variations in the velocity of the fluid stream, and this invention seeks to provide such a particle detector and a method for its use.

SUMMARY OF THE INVENTION

This invention provides apparatus for measuring the concentration of solid particles in a fluid stream, this apparatus comprising means for producing a sub-stream of fluid having a substantially constant velocity independent of the fluid stream, a triboelectric charging surface disposed so that particles in the sub-stream can impact upon the surface, thereby effecting triboelectric charging of these particles, and charge measuring means for measuring the charge produced on the particles by said impacts.

This invention also provides a method for measuring the concentration of solid particles in a fluid stream which is susceptible to changes in velocity, this method comprising producing a sub-stream of the fluid having a velocity which is substantially constant and independent of the velocity of the main fluid stream. This sub-stream of fluid is allowed to come into contact with a triboelectric charging surface, thereby effecting triboelectric charging of the particles in the sub-stream, and thereafter the charge produced upon the particles by their impacts on the triboelectric charging surface.

DETAILED DESCRIPTION OF THE INVENTION

I believe (although this has not previously been reported in the literature and this invention is in no way limited by this belief) that the main reason for the increase in apparent dust concentration with fluid stream velocity experienced with prior art triboelectric particle detectors is that the lower limit on the size of particle detected decreases as the velocity of the fluid stream increases. As already mentioned, triboelectric particle detectors do not detect particles below a certain size, and indeed this is one of the advantages of such detectors. This ability of triboelectric particle detectors to ignore very small particles arises because only particles which actually impact upon the triboelectric charging surface undergo charging and only the particles which experience such triboelectric charging are measured by the detector. If one considers a stream of fluid containing solid particles approaching a triboelectric charging surface (which of necessity causes a deflection in the path of the fluid phase), it will be seen that two opposing forces act upon the solid particles in the fluid as the fluid is deflected by the surface. The inertia of a solid particle will tend to make it follow a straight path along the line which it was following before deflection of the fluid occurred. However, frictional forces imposed by the fluid phase will tend to make the particle follow the fluid flow around the surface. In the case of very small particles, the ratio of frictional to inertial forces is large so that such small particles essentially follow the movement of the fluid phase and do not come into contact with the surface. On the other hand, in the case of large particles the ratio of frictional to inertial forces is much smaller, and thus the inertial forces tend to prevail so that the particle proceeds substantially in its original direction and strikes the surface. Thus, the very small particles do not undergo charging by contact with the surface, whereas large particles are so charged. However, the magnitude of the inertial forces on any particular particle is dependent upon the rate at which the fluid stream approaches the charging surface, whereas the frictional forces acting upon the particle are effectively independent of fluid stream velocity. Thus, for any particular size of particle the ratio of inertial to frictional forces will increase as the velocity of the fluid stream increases, and thus the minimum size of particle which will undergo contact with the charging surface decreases as the fluid stream velocity increases. Accordingly, even though the concentration of particles in a fluid stream remains constant, increase in velocity of the fluid stream adjacent the charging surface will increase the number of particles striking the surface and undergoing charging, and the resultant increase in charging will cause an apparent increase in the particle concentration measured by the triboelectric particle detector. In other words, the apparent increase in particle concentration with fluid stream velocity experienced with prior art triboelectric charge detectors arises because such detectors tend to "see" more particles as the fluid stream velocity increases. In the instant apparatus and method, the velocity of the sub-stream of fluid passing the triboelectric charging surface is rendered substantially constant even when the velocity of the main fluid stream varies, and thus the minimum size of particle detected remains constant regardless of the main fluid stream velocity.

The means for producing the sub-stream of fluid in the instant application and method may have a variety of forms. For example, the sub-stream may be provided by a constant-volume pump. Those skilled in the art will be aware of a variety of peristalsic pumps which will pump at constant volume, and thus product a constant velocity of gas past the electrode, regardless of the fluid velocity in the main stream. When such a constant volume pump is to be used, it is desirably arranged so that the sub-stream of fluid passes through the pump after it has passed the electrode (i.e. the pump is disposed downstream of the electrode) so that the proper functioning of the electrode will not be disturbed by charges placed upon the particles as they pass through the pump; it will be apparent to those skilled in the art that pumps are capable of effecting triboelectric and other charging of particles in fluid passing therethrough.

However, the preferred means for producing the sub-stream of gas is an orifice member having walls defining a critical flow orifice through which the sub-stream of fluid can pass. It is of course necessary that, when a critical flow orifice is employed, the apparatus include means for producing a pressure drop across this orifice sufficient to ensure critical flow therethrough, since only such critical flow will make the fluid velocity past the electrode independent of the fluid velocity in the main stream. It is well known to those skilled in the art that (at least for the sizes of critical flow orifices practically useful in the instant apparatus and method) the pressure drop needed to ensure critical flow through the orifice is effectively independent of orifice size and is approximately 0.5 atmosphere. Since this pressure drop is greater than that which is naturally present in vehicle air intake systems, and in most of the other systems in which the apparatus and method are likely to be used, in most cases when the instant apparatus includes a critical flow orifice it will be necessary to provide a pump to establish the necessary pressure drop across the critical flow orifice. For the same reasons as discussed above with reference to constant volume pumps, it is desirable that this pump be installed downstream from the electrode of the instant apparatus. A pump used in conjunction with a critical flow orifice need not meet any exacting performance requirements as regards pressure difference across the pump, since the flow through the orifice will remain constant provided the pump maintains a sufficient pressure drop across the orifice to ensure critical flow therethrough. A commercially available vacuum pump may thus be used in conjunction with the critical flow orifice. On the other hand, when using a constant volume pump as the sub-stream producing means of the instant apparatus, it is necessary that this pump be able to maintain a constant flow despite wide variations in the velocity of the main fluid stream. It is believed that the use of a critical flow orifice and a pump as the sub-stream producing means will probably lead to better performance than the use of a constant volume pump alone.

When the instant apparatus includes a pump, either a pump used in conjunction with a critical flow orifice or a constant volume pump used without an orifice, the pump may be driven in any convenient manner. For example, the pump may be driven by a separate prime mover, such as an electric motor. However, when the instant apparatus is to be used on a vehicle, it may be more convenient to drive the pump via a belt drive from the usual pulley system incorporated in internal combustion engines.

In most practical applications, the critical flow orifice should have a diameter not exceeding 1 millimeter and preferably not exceeding 0.5 millimeter. Those skilled in the art will be aware of various types of orifice members which can be used to provide the critical flow orifice in the instant apparatus; typically, such orifice members comprise a cylinder sized to fit within a conduit along which the sub-stream of fluid is to pass, this cylindrical member having a cylindrical aperture passing axially therethrough. Whatever type of orifice member is employed, the instant apparatus is very desirably designed so that the critical flow orifice points directly at the triboelectric charging surface in order to ensure a maximum degree of charging and thus optimum sensitivity for the apparatus. When the charge measuring means of the instant apparatus includes an electrode projecting into the sub-stream of fluid, the triboelectric charging surface may be part of the surface of the electrode itself. However, a triboelectric charging surface separate from the electrode may alternatively be employed. For example, the apparatus may include a conduit extending from the critical flow orifice to the electrode, and this conduit may be curved to provide a triboelectric charging surface on the radially outward portion of the internal surface of the conduit. Obviously, if the charge measuring means uses a type of electrode which does not project substantially into the sub-stream of fluid (for example, if the electrode has the form of a cylinder lying closely adjacent the internal walls of a cylindrical conduit), it may be necessary to employ a triboelectric charging surface separate from the surface of the electrode.

In variants of the instant apparatus which do not employ a critical flow orifice, it is obviously not possible to arrange for direction of the sub-stream of fluid onto the triboelectric charging surface by means of such an orifice. Accordingly, in order to increase the efficiency of triboelectric charging, it may be desirable to use either a relatively narrow conduit along which the sub-stream of gas can pass to the triboelectric charging surface, or else form a throat in the conduit adjacent the triboelectric charging surface, in order to direct the sub-stream onto the triboelectric charging surface in the same manner as when a critical flow orifice is employed.

It is desirable to avoid an accumulation of particles on the triboelectric charging surface, since such an accumulation will interfere with the proper charging of particles impacting upon the surface. If the material of the triboelectric charging surface is such that accumulation of particles on the surface becomes a problem, an appropriate coating may be applied to the surface to prevent such an accumulation. However, it is also important to avoid accumulation of charge on the triboelectric charging surface, since this would interfere with the tracks which particles approaching the surface take, and thus the coating material should not be one which permits a charge accumulation thereon.

The charge measuring means of the instant apparatus will normally comprise an electrode on which a charge is developed, either by impact of the particles upon the electrode (where the electrode surface itself comprises the triboelectric charging surface) or by the passage of particles near the electrode (where a separate triboelectric charging surface is provided upstream of the electrode), together with appropriate circuitry for measuring the charge developed on the electrode. Those skilled in the art will appreciate that, although the instant apparatus and method measure the triboelectric charge produced on the particles in the sub-stream and results of the impacts of these particles upon the triboelectric charging surface, the exact mode in which these charges are measured differs depending upon whether the triboelectric charging surface is the surface of the electrode used as the charge measuring means or whether the electrode is separate from the triboelectric charging surface. Where the surface of the electrode itself constitutes the triboelectric charging surface, the charges actually measured are the charges produced on the electrode by the triboelectric charging process, these charges on the electrode being equal and opposite to those produced on the particles. On the other hand, where an electrode separate from the triboelectric charging surface is employed, this electrode actually measures the charges on the particles themselves. Obviously, although the two types of apparatus thus measure the charge produced on the particles in different ways, they both produce a signal properly representative of the charge on the particles.

Where a triboelectric charging surface separate from the electrode is provided, the associated circuitry may be of either a current measuring type or a pulse measuring type. The current measuring type circuitry relies upon the actual placement of charge upon the electrode by the particles and simply allows this charge to flow (to ground), the magnitude of the current through the circuitry indicating the amount of charge being placed upon the electrode. In contrast, pulse detecting circuitry does not rely upon the particles actually contacting the electrode; instead, it relies upon the charges induced on the electrode as particles pass the electrode. As a charged particle approaches the electrode, it induces an opposite charge on the electrode which gradually increases from zero to a value approximately equal to the charge on the particle, thereby inducing a current from the electrode through the pulse measuring circuitry which increases to a maximum value and then drops to zero as the charge induced on the electrode reaches its maximum value. Once the charged particles pass the electrode, the induced charge on the electrode begins to diminish and eventually drops to zero, thereby producing a current through the pulse measuring circuitry in the opposite direction to the current produced as the particle approaches the electrode. Thus, each separate charged particle or group of charged particles will produce two pulses of opposite polarity as they pass the electrode, and these pulses are measured by the pulse measuring circuitry to indicate the concentration of particles in the fluid stream.

However, one disadvantage of such pulse counting circuitry is that a cloud of particles bearing substantially uniform charges will produce only a single pulse as the leading of the cloud first approaches the electrode and a single pulse as the trailing edge of the cloud leaves the electrode. Thus, to accurately measure the concentration of particles in a fluid stream containing many such particles, the pulse counting circuitry may be required to be of a relatively complicated type which can take account not only of the number of pulses generated but also of the interval between the two spaced pulses of opposite polarity produced by the particle cloud, with some form of integration device to calculate the total number of particles passing the electrode in such a cloud. Fortunately, if an instant apparatus containing pulse counting circuitry is only to be used to detect failure of a filter arrangement in a vehicle air intake system, such refinement will normally be unnecessary; dust clouds of uniform charge concentration are comparatively rare, the charge concentrations within such a dust cloud tending to vary and thus produce many pulses, so that if the apparatus is only to be used on a "yes/no" basis to detect failures in the air filtration system, relatively simple pulse measuring circuitry should normally yield sufficiently good information.

In order for the instant apparatus to accurately measure the concentration of particles in the fluid stream, it is of course necessary that the charges measured by the charge measuring means be substantially those placed upon the particles by the triboelectric charging surface. I have found that often natural dust and similar particles already bear substantial charges and thus unless these natural charges are neutralized before the particles pass the triboelectric charging surface, the readings from the charge measuring means will be inaccurate. Accordingly, the instant apparatus preferably includes a charge neutralizing device for neutralizing pre-existing charges on the particles before the particles pass the triboelectric charging surface, this charge neutralizing device conveniently being an alternating current ionizer. It will be appreciated that, although the charge neutralizing device must be upstream of the triboeletric charging surface, it does not matter it is upstream or downstream of the critical flow orifice, although to reduce the size of the charge neutralizing device to a minimum it is desirable to position this device so that it only has to neutralize the charges on particles which will pass through the critical flow orifice, rather than on the whole stream of gas which is being monitored.

From a purely theoretical point of view, it does not matter what happens to the sub-stream of fluid after it has passed the electrode (and the pump downstream of the electrode if such a pump is employed). Thus, for example, the sub-stream of fluid could simply be allowed to leave the apparatus back into the atmosphere. However, to avoid potential contamination of the apparatus by dirt and other particulate material when no fluid flow is taking place therethrough, it will normally be desirable to design the apparatus so that the sub-stream of fluid rejoins the main fluid stream. Since the main stream of fluid will normally be relatively free of contamination, such rejoining of the sub-stream to the mainstream will tend to prevent contamination of the instant apparatus when no fluid flow is occuring.

As already mentioned, the instant apparatus may be used in a filtering system to check that the filtering system is performing properly. Thus, the instant apparatus may include a filter for removing particles from the fluid stream. The instant apparatus may also comprise a fluid receiving device which receives the fluid stream and cut-off means for preventing damage to the fluid receiving means whenever the charge measuring means indicates that the concentration of particles in the fluid exceeds a predetermined value. Such a cut-off means may typically take the form of a servomechanism responsive to the charge measuring means and arranged to take action to prevent damage to the fluid receiving device whenever the charge measuring means indicates the presence of a predetermined concentration of particles in the fluid flow past the electrode. For example, when the fluid receiving device is an engine, the cut-off means may typically comprise a valve for blocking the flow of gas from the filtration system to the engine and may also include means for stopping the engine e.g. by interrupting the high tension current in the case of an engine relying upon spot ignition, or by interrupting the fuel supply in the case of a diesel engine. It is desirable that the cut-off means also include means for providing a warning signal such as a visible or audible alarm; when the instant apparatus is being used on a vehicle, it is of course desirable that a visible alarm be placed on the dashboard adjacent the normal instruments so that it will be readily visible to the driver.

When the instant apparatus is employed in an air intake system with a filter or other dust-removing device which is subjected to failure and the charge measuring means employs an electrode projecting into the air stream, upon failure of the filter gas containing a very large concentration of particles may pass the electrode, with the risk that substantial quantities of particles may be deposited upon the electrode. Although the quantity of dust particles deposited upon the electrode after a single filter failure is not likely to greatly affect the operation of the electrode, after repeated filter failure a sufficiently large quantity of dust particles may be deposited upon the electrode to reduce the sensitivity and/or reproducability of operation of the apparatus. Accordingly, it is recommended that after each filter failure the electrode be inspected and, if necessary, cleaned to ensure proper operation of the instant apparatus.

Figure 1:
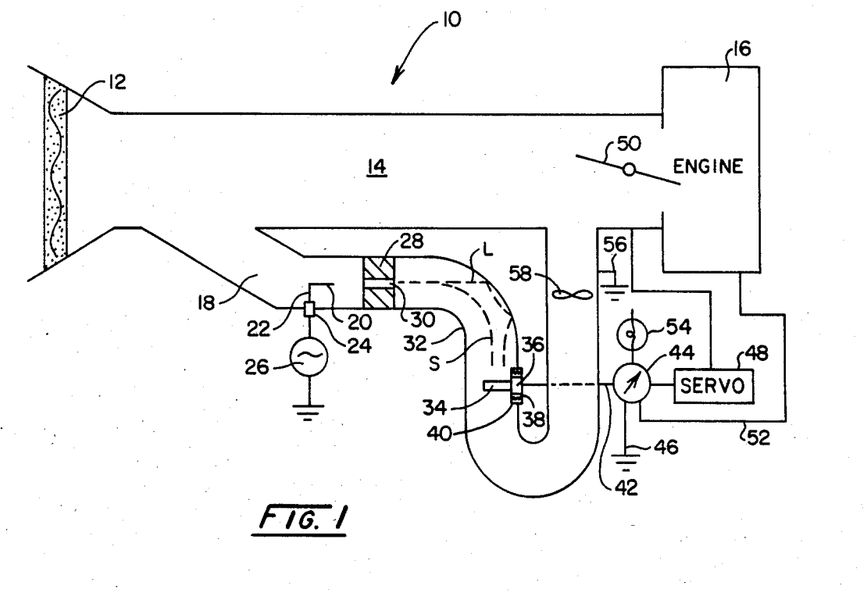
FIG. 1 is a highly schematic section through a first apparatus of the invention.

The first embodiment of the invention shown schematically in FIG. 1 of the accompanying drawings is a vehicle air intake system. The apparatus (generally designated 10) comprises an air filter 12, an air intake conduit 14 which receives the stream of gas passing through the filter 12 and an engine 16 which receives the gas from the conduit 14.

A branch conduit 18 diverges from the conduit 14 downstream of the filter 12. The size of the branch conduit 18 relative to the conduit 14 is greatly exaggerated in FIG. 1 for the sake of clarity; as will be apparent to those skilled in the art, only a very small branch conduit is necessary to supply sufficient gas to the critical flow orifice described below—typically, a branch conduit having an internal diameter of about 3 mm. should be sufficient. In the branch conduit 18, which is of circular cross section, there is provided an alternating current ionizer comprising a needle 20 disposed axially within the branch conduit 18, a support member 22 which holds the needle 20 in position and which passes through the wall of the branch conduit 18, being insulated therefrom by an insulator 24, and a source 26 of alternating potential.

Downstream from the needle member 20 is disposed an orifice member 28 which extends completely across the branch conduit 18. The orifice member 28 has a critical flow orifice 30 extending axially therethrough.

Downstream of the alternating current ionizer the branch conduit 18 is bent to form a curved section 32. As indicated by the particle track L in FIG. 1, particles of sufficient diameter to be detected by the apparatus which pass through the critical flow orifice 30 will proceed substantially linearily from the outlet end of the orifice 30 and will thus strike the radially outward section of the internal wall of the curved section 32; thus, this radially outward portion of the internal wall of the curved section 32 acts as the triboelectric charging surface of the apparatus and effects triboelectric charging of the particles which impact thereon. On the other hand, as shown by the particle track S in FIG. 1 particles of small diameter will follow the air flow through the curved section 32 and thus will not strike the charging surface nor undergo charging.

Downstream from the curved section 32 of the branch conduit 18, an electrode 34 is mounted in an aperture in the wall of the conduit 18 by means of a cylindrical insulator 36, which serves to electrically insulate the electrode 34 from the wall of the branch conduit 18 (the branch conduit 18 is formed of metal). The cylindrical wall of the insulator 36 is fixedly attached to a cylindrical metal sleeve 38, which surrounds the insulator 36 and bears an external screw thread. This external screw thread engages a corresponding internal screw thread within a cylindrical sleeve 40 welded to and extending radially of the branch conduit 18. The screw thread engagement between the two sleeves 38 and 40 permits the electrode 34 to be readily moved from the branch conduit 18 when this is desirable for cleaning or replacement of the electrode 34.

A wire 42 extends from the electrode 34 through the insulator 36 to a current measuring device 44 located outside the branch conduit 18, the side of the current measuring device 44 remote from the electrode 34 being grounded by a line 46. The current measuring device 44 controls a cut-off device in the form of a servomechanism 48 which is arranged to close a butterfly valve 50 disposed within the conduit 14; as shown in FIG. 1, the branch conduit 18 rejoins the conduit 14 upstream of the valve 50. The current measuring device 44 is also connected to a line 52 which can be used to shut down the engine 16, e.g. by interrupting an ignition circuit therein, and to a warning lamp 54 disposed on the dashboard of the vehicle on which the apparatus is mounted. The branch conduit 18 is itself grounded by a line 56. A vacuum pump 58 is disposed in the branch conduit 18 downstream of the electrode 34. This vacuum pump produces a partial vacuum in the portion of the branch conduit 18 lying between the orifice member 28 and the pump 58, thereby ensuring that the pressure drop across the orifice 30 is sufficient to cause critical flow therethrough.

The electrode 34 has the form of an elongate, cylindrical rod approximately equal in length to the radius of the branch conduit 18 and extends radially of the conduit (i.e. perpendicular to the gas flow along the conduit 18) so that the free end of the electrode 34 lies approximately on the axis of the branch conduit 18. The electrode 34 is provided with a substantially rectangular cut-out extending radially therethrough in a direction parallel to the air flow along the branch conduit 18. It has been found that this form of electrode gives good sensitivity without offering substantial resistance to air flow along the branch conduit 18.

The apparatus 10 operates as follows. When the engine 16 is operating, air is drawn through the filter 12 and along the conduit 14. Air from the conduit 14 enters the branch 18 and, as it passes the needle member 20, the ions of both charges emitted from the needle member 20 neutralize substantially all charges on the incoming particles. Thereafter, critical flow of this air occurs through the critical flow orifice 30 because of the pressure drop across this orifice 30. Accordingly, the velocity of air flow through the critical flow orifice 30 is independent of engine speed. After passing through the critical flow orifice 30, the air and the entrained particles therein pass to the curved section 32 of the branch conduit 18 where the larger particles in the air are triboelectrically charged, as indicated by the tracks L in FIG. 1. After one or more collisions with the radially outward part of the internal wall of the curved section 32, the momentum of the large particles parallel to the axis of the critical flow orifice 30 will be destroyed and thus the larger particles will travel down the branch conduit 18 past the electrode 34. The collisions between the particles and the walls of the curved section 32 will cause friction between the particles and the wall, resulting in triboelectric charging of the particles, which will thus be charged as they pass the electrode 34.

Accordingly, notwithstanding the neutralization of all existing charges by the ionizer assembly, the air flow past electrode 34 will contain charged particles which have undergone triboelectric charging in the curved section 32. The flow of air containing the charged particles along the branch conduit 18 past the electrode 34 creates a flow of space charge within this conduit and this space charge deposits charge particles on the electrode 34, thereby causing a current flow from the electrode 34 through the current measuring means 44 and the line 46 to ground; however, since the small particles will tend to follow the air flow along the branch conduit 18, they will not undergo triboelectric charging within the curved section 32 and the current passing from the electrode 34 to ground will be determined only by the concentration of the large particles in the air flow. While the filter 12 is operating normally, the current passing through the current measuring means will remain a predetermined level and the servomechanism 48 will keep the valve 50 in the open position shown in FIG. 1 so that air flow to the engine 16 is not interrupted. If, however for any reason, (e.g. perforation of the filter 12) the concentration of large particles in the air flow along the branch conduit 18 becomes too great, the current passing through the current measuring device 44 will exceed the predetermined value. When the current measuring device 44 registers this excessive current, it sends a signal to the servomechanism 48 which closes the valve 50, thus cutting off the flow of dirty air to the engine 16 before the engine can become damaged. In addition, the current measuring device 44 sends a signal along the line 52 to shut down the engine in an appropriate manner. Finally, the current measuring device 44 causes a current flow through the lamp 54 thus illuminating this lamp and advising the driver of the vehicle that the filter 12 has failed.

It will be appreciated that, when the instant apparatus is being used in certain types of vehicles (for example, highway trucks), the sudden shut down of the engine 16 just described could be dangerous. Accordingly, when the engine 16 is of a type which can tolerate a short period of operation on dusty air without significant damage, it may be desirable to use a form of current measuring device 44 which gives an instant warning of failure of the filter 12 (by illuminating the lamp 54), but does not interrupt the air flow to the engine, thus allowing the driver to stop the vehicle without the engine being shut down.

Figure 2:
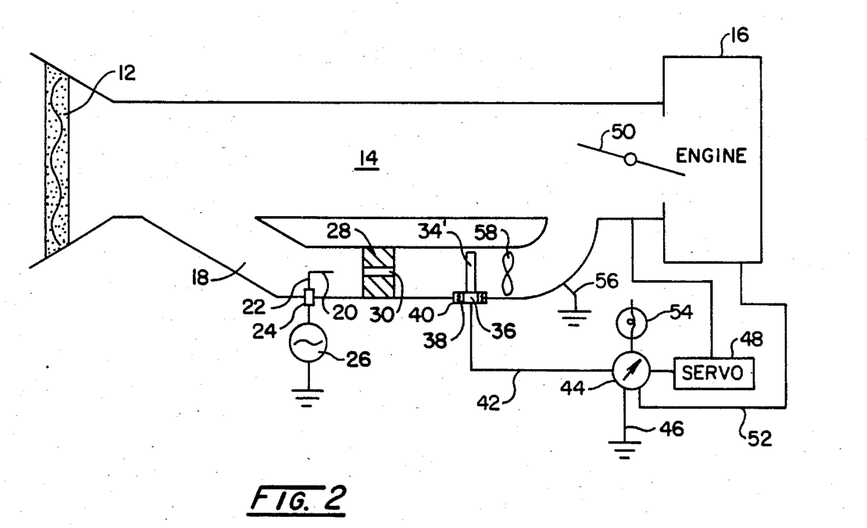
FIG. 2 is a highly schematic section through a second apparatus of the invention.

The second embodiment of the invention shown schematically in FIG. 2 is very similar to that shown in FIG. 1 except that the branch conduit 18 is not curved; instead, the surface of the electrode 34' itself acts as the triboelectric charging surface i.e. triboelectric charging of the large particles in the air flow along the branch conduit 18 is effected by collision between the particles and the electrode 34'. Accordingly, the electrode 34' is made somewhat longer than the electrode 34 shown in FIG. 1 in order that the axis of the critical flow orifice 30 will pass substantially through the center of the electrode 34'. Also, since charging of the particles actually requires collisions with the electrode 34', no aperture is provided extending through the electrode 34' since the presence of such an aperture would obviously reduce the number of particles undergoing collisions with the electrode. Finally, those skilled in the art will appreciate that, although the electrode 34', like the electrode 34, produces a flow of current through the current measuring device 44, the actual source of this current is somewhat different; whereas the current produced by the electrode 34 is due to loss of charge from previously-charged particles depositing on the electrode, the current flow from the electrode 34' is due to the dispersal of charge generated at the surface of the electrode 34' when the particles strike the surface.

Figure 3:
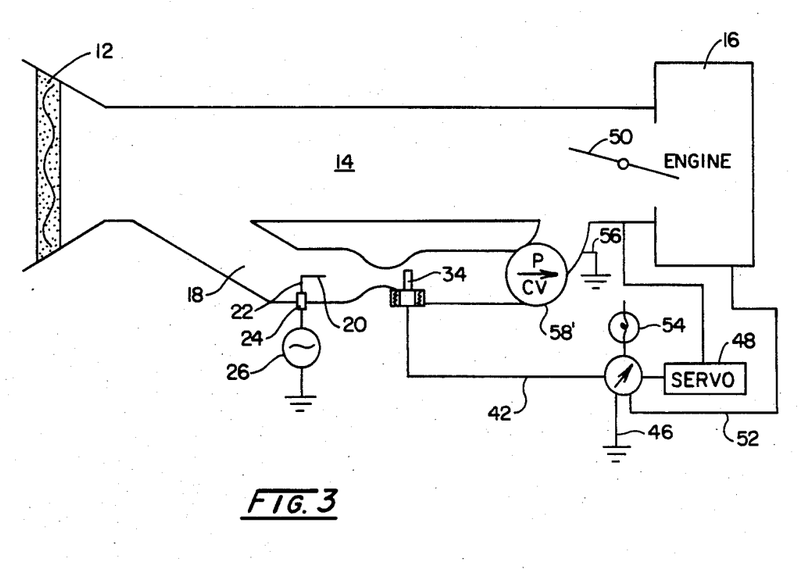
FIG. 3 is a highly schematic section through a third apparatus of the invention.

The third embodiment of the invention shown in FIG. 3 is closely similar to that shown in FIG. 2 but employs a different type of sub-stream producing means. The orifice member 28 and the vacuum pump 58 are eliminated. Instead, the production of the sub-stream of fluid is effected by a constant volume pump 58', which is disposed downstream of the electrode 34 in substantially the same position as the vacuum pump 58 in FIG. 2. This constant volume pump 58' causes a sub-stream of fluid to pass the electrode 34 at a substantially constant velocity independent of the rate of flow of the mainstream of fluid along the conduit 14. In order to ensure efficient triboelectric charging at the electrode 34, the branch conduit 18 is narrowed to form a throat adjacent the electrode 34; this throat serves to direct the sub-stream of fluid directly at the electrode 34, in substantially the same manner as the orifice 30 in the apparatus shown in FIG. 2.

Figure 4:
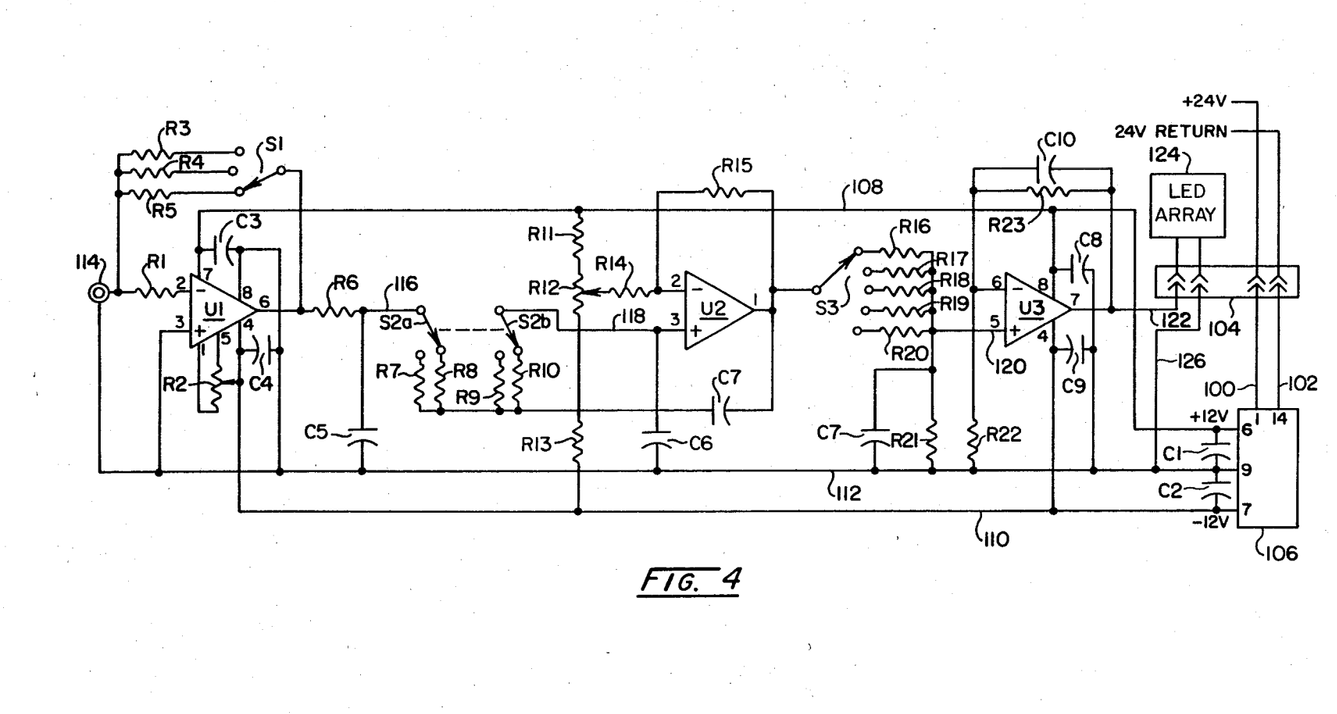
FIG. 4 is a partial circuit diagram of the current measuring device shown in FIGS. 1, 2 and 3.

FIG. 4 shows a partial circuit diagram of the current measuring device 44 shown in FIGS. 1, 2 and 3. FIG. 4 shows the amplifying part of the current measuring device connected to a bar graph light emitting diode (LED) array which provides a visual indication of the current passing through the current measuring device and which can, if desired, be provided instead of or in addition to the warning lamp 54. The switching circuits necessary to activate the servomechanism 48, the warning lamp 54 and the engine control line 52 are not shown in FIG. 4 since they are entirely conventional and appropriate circuits will readily be apparent to those skilled in the art.

The circuit shown in FIG. 4 is powered from a 24 V D.C. supply supplied between a positive supply line 100 and a return line 102. The lines 100 and 102 are connected, via a four-pin connector 104, to pins 1 and 14 respectively of a voltage stabilization circuit 106, which is an Integrated Circuits DIP 24 1212DB integrated circuit. This integrated circuit produces a +12 V output on its pin 6 which is connected to a positive supply line 108, a −12 V output on its pin 7 which is connected to a negative supply line 110, and a common or ground output at its pin 9 which is connected to a ground line 112. A smoothing capacitor C1 is connected between the positive supply line 108 and the ground line 112, while a second smoothing capacitor C2 is similarly connected to the negative supply line 110 and the ground line 112.

The input to the current measuring device from line 42 (FIG. 1, 2 or 3) is received at a socket 114, one terminal of this socket being connected via a resistor R1 to the negative input (pin 2) of an integrated circuit U1. (To provide the necessary input impedance, resistor R1 preferably has a value of the order of $10^{10}$ ohms.) This integrated circuit U1 is an Intersil ICH 8500 ACTV amplifier circuit, which is an electrometer amplifier circuit having a very high input impedance. The positive input (pin 3) of integrated circuit U1 and pin 8 thereof are connected directly to the ground line 112, pin 4 is connected directly to the negative supply line 110, and pin 7 directly to the positive supply line 108. A capacitor C3 is connected between pins 7 and 8 (thus bridging the positive supply and ground lines 108 and 112 respectively) while a further capacitor C4 is connected between pins 4 and 8, thus bridging the negative supply and the ground lines 110 and 112 respectively. Finally, pins 1 and 5 of integrated circuit U1 are bridged by resistance R2, which forms a part of a potentiometer, the movable terminal of this potentiometer being connected to the negative supply line 110.

The output from integrated circuit U1 appears at pin 6. A variable feedback loop is provided for integrated circuit U1, the output from pin 6 of U1 being supplied to a three-position switch S1 which can be used to place any one of three different resistors R3, R4 and R5 in series with resistor R1 between pins 6 and 2 of integrated circuit U1. By selecting different ones of the resistors R3, R4 and R5, the range of current measured by the circuit can be varied. The output of pin 6 of U1 is also supplied via a resistor R6 to a line 116 which is connected to the removable terminal of a two-position selector switch S2a. This switch can be used to place one of the two resistors R7 and R8 in series with R6. The common output of R7 and R8 is connected to a common input of two resistors R9 and R10, one of which can be selected by a switch S2b which is ganged with S2a so that either R7 or R9 or R8 and R10 can be placed in series with R6. The output from switch S2b is conveyed by a line 118 to a positive input (pin 3) of an integrated circuit U2. Capacitors C5 and C6 connect the ground line 112 to the lines 116 and 118 respectively; thus, C5 and C6, together with the resistors R7/R8 and R9/R10 respectively, form two RC circuits which effect low-pass filtering of the output from U1 before it reaches U2.

The integrated circuit U2 actually comprises one-half of a Texas Instruments TLO 72 double linear amplifier integrated circuit, the other half of this double amplifier being the integrated circuit U3 described below. As is conventional, power supply connections to the double amplifier are only shown on one of the amplifier components, in this case U3. To provide a variable negative input for U2, resistors R11, R12 and R13 are arranged in series as a voltage divider between the positive and negative supply lines 108 and 110 respectively and an appropriate voltage, which can be varied by the operator, is tapped from R12 and fed via a resistor R14 to the negative input (pin 2) of U2. This tapping of the variable voltage from R12 enables the amplifier U2 to be adjusted for any offset on the incoming signal due to e.g. small leakage currents even when no dust is present in the air flowing along the branch conduit 18 (FIG. 1, 2 or 3). The output of U2 appears at pin 1 thereof and, to establish appropriate feedback, this output is fed via a resistor R15 to pin 2 thereof and via a capacitor C7 to the common input of resistors R9 and R10. The output from pin 1 of U2 is also fed to the movable terminal of a five-position selector switch S3, which places one of five different resistors R16, R17, R18, R19 and R20 between the output of U2 and a line 120 connected to the positive input (pin 5) of the aforementioned integrated circuit amplifier U3. An RC circuit comprising a capacitor C7 in parallel with a resistor R21 is connected between the line 120 and the ground line 112. The negative input (pin 6) of U3 is connected via a resistor R22 to the ground line 112. The positive and negative power supply inputs, pins 8 and 4 respectively, of U3 are connected to the positive and negative supply lines 108 and 110 respectively, those pins 8 and 4 are also connected via capacitors C8 and C9 respectively to the ground line 112. The switch S32 and the associated resistors R16/R20 allow adjustment of the overall gain provided by the amplifiers U2 and U3.

The output from U3 appears at pin 7 thereof. To provide proper feedback, this output is fed back via an RC circuit comprising a capacitor C10 connected in parallel with a resistor R23 to the negative input (pin 6) of U3. The output from U3 is also fed via a signal line 122 and the four-pin connector 104 to a bar graph LED array 124, which is of the commercially available National Semicnductor Model NSM 3914 type. A signal return line 126 from the array is connected by the four-pin connector 104 to the ground line 112.

It will thus be seen that the circuit shown in FIG. 4 provides a three-stage amplification of the incoming signal from the socket 114, these three stages of amplification being effected by the integrated circuits U1, U2 and U3 respectively. The circuit provides for adjustment of range, offset and gain by means of the switch S1, the variable voltage applied to the negative input of amplifier U2, and the switch S3 respectively and also provides for filtering of the incoming signals by the RC circuits formed by the capacitors C5 and C6 in association with the resistors R7/R8 and R9/R10 respectively. Thus, the curcuit shown in FIG. 4 converts the very small currents, of the order of $10^{-12}$ to $10^{-13}$ amps. flowing through the resistor R1 and the socket 114 to a varying voltage on line 122 sufficient to drive the LED array 124.

The circuit shown in FIG. 4 is an experimental prototype and is deliberately provided with variable range, filter and gain settings in order to enable it to be used with a variety of types of apparatus of the invention. Those skilled in the art will appreciate that production models of such a circuit, intended only for use with one particular type of electrode in a specific vehicle or other environment, will not normally require such variability, thus permitting considerable simplification of the circuitry; in such an invariable production model, a single resistor could replace the resistors R3, R4 and R5 and the switch S1, a second single resistor could replace the switch S2 and the resistors R7, R8, R9 and R10, while a third single resistor could replace the switch S3 and the resistors R16–R20.

As mentioned above, the embodiments of the invention such as those shown in FIG. 1 where the triboelectric charging surface is separate from the electrode of the charge measuring means, the circuitry of the charge measuring means (i.e. the current measuring device 44) may be either of a current measuring type or of a pulse detecting type.

Although the circuit shown in FIG. 4 has been described above as a current measuring circuit, it can readily be modified to act as a pulse detecting circuit merely by changing the values of certain components. As will be appreciated from the description given above as to the mode of operation of both the pulse counting and current measuring types of the instant apparatus, the current actually induced in a line connecting the electrode 34 (FIG. 1) to ground will be the same in both cases, the signal comprising a direct current caused by the deposition of charged particles on the electrode, but superimposed upon this direct current will be "spikes" or pulses produced by induction of the charges on the electrode as dust particles pass the electrode 34 without being deposited thereon. Thus, a current measuring circuit used in the instant apparatus should be equipped with a low-pass filter with a cut-off frequency sufficiently low to eliminate the pulses in the incoming signal; in practice, this cut-off frequency is preferably about 1 Hz. In the circuit shown in FIG. 4, a cut-off frequency of about 1 Hz. can be achieved by using resistors R8 and R10 of about 1 megaohm, giving C5 a value of 2.2 microfarad and capacitor C6 a value of 1 microfarad. In fact, the cut-off frequency of the circuit shown in FIG. 4 is in practice regulated not only by the RC circuits formed by the capacitors C5 and C6 together with the resistors R7–R10, but also by the input resistor R1. To provide a high input resistance to the circuit, we prefer to make the resistor R1 about $10^{10}$ ohms, and such a resistor will have an inherent capacity of about 10 picofarad. Thus, resistor R1 alone acts as a filtering RC circuit with a cut-off frequency of around 2 Hz.

Obviously, to modify the circuit shown in FIG. 4 so that it acts as a pulse counting circuit, it will be necessary to raise the cut-off frequency of the circuit. This may conveniently be done by reducing R1 to about $10^8$ ohms, and reducing resistors R8 and R10 to about 100 kilohms thereby raising the cut-off frequency to around 10 Hz. Those skilled in the art will also appreciate that it will be necessary to pass the output from the circuit shown in FIG. 4 to a conventional pulse counting device rather than to a bar graph array.

The apparatus of the invention is small, rugged, relatively insensitive to vibration, requires little power and is able to distinguish between large and small particles in the gas flow, thus avoiding false alarms due to very small particles which will not harm a gas-using device attached thereto.

It will be apparent to those skilled in the art that numerous changes and modifications can be made in the preferred embodiments of the instant apparatus and method already described without departing from the scope of the invention. Accordingly, the foregoing description is to be construed in an illustrative and not in a limitative sense, the scope of the invention being defined solely by the appended claims.

We claim:

1. Apparatus for measuring the concentration of solid particles in a fluid stream, said apparatus comprising:
means for producing a sub-stream of fluid, means for producing a substantially constant velocity in said sub-stream which is independent of the velocity of said fluid stream;
a triboelectric charging surface disposed such that particles in said sub-stream can impact upon said surface, thereby effecting triboelectric charging of said particles impacting upon said surface; and
charge measuring means for measuring the charge produced on said particles by said impacts.

2. Apparatus according to claim 1 wherein said charge measuring means includes an electrode and said triboelectric charging surface comprises at least part of the surface of said electrode.

3. Apparatus according to claim 1 wherein a conduit is provided to receive said part of said fluid flow and wherein said triboelectric charging surface comprises a curved portion of the internal surface of said conduit.

4. Apparatus according to claim 1 wherein said sub-stream producing means comprises a conduit member having walls defining a critical flow orifice through which said sub-stream of fluid can pass, said orifice being upstream of the triboelectric charging surface, and means for producing a pressure drop across said orifice sufficient to ensure critical flow therethrough.

5. Apparatus according to claim 4 wherein said means for producing a pressure drop comprises a pump through which said sub-stream of fluid is arranged to pass after said sub-stream has passed said charge measuring means.

6. Apparatus according to claim 4 wherein said critical flow orifice has a diameter not exceeding about 1 mm.

7. Apparatus according to claim 6 wherein said critical flow orifice has a diameter not exceeding about 0.5 mm.

8. Apparatus according to claim 1 wherein said sub-stream producing means includes a constant volume pump.

9. Apparatus according to claim 8 wherein said pump is arranged so that said sub-stream of fluid will pass through said pump after said sub-stream has passed said charge measuring means.

10. Apparatus according to claim 1 further comprising a charge neutralizing device for neutralizing pre-existing charges on said particles before said particles impact upon said triboelectric charging surface.

11. Apparatus according to claim 10 wherein said charge neutralizing device comprises an alternating current ionizer.

12. Apparatus according to claim 1 wherein said sub-stream producing means comprises:
a conduit member formed of electrically-conductive material and having walls defining a conduit through which said fluid can flow;
an electrode at least part of which is disposed within said conduit;
an insulator disposed between said conduit member and said electrode, thereby electrically insulating said electrode from said conduit member;
current measuring means electrically connected to said electrode; and
potential maintaining means for maintaining said conduit member and said electrode at substantially the same potential.

13. Apparatus according to claim 12 wherein said potential maintaining means comprises a connection between said conduit member and ground and a connection between said current measuring means and ground such that current from said electrode will flow through said current measuring means to ground.

14. Apparatus according to claim 12 wherein said electrode has the form of an elongate rod extending part-way across said conduit in a direction substantially perpendicular to the flow of fluid therealong.

15. Apparatus according to claim 1 further comprising a filter for removing particles from said fluid before it passes said electrode.

16. Apparatus according to claim 1 further comprising a fluid receiving device which receives said fluid stream and cut-off means for preventing damage to said fluid receiving means wherever said charge measuring means indicates that the concentration of particles in said fluid exceeds a predetermined value.

17. Apparatus according to claim 16 wherein said fluid is a gas and wherein said fluid receiving device is an engine and said cut-off means comprises means for preventing said gas stream from reaching said engine.

18. Apparatus according to claim 16 wherein said cut-off means further comprises means for stopping said engine.

19. Apparatus according to claim 17 wherein said cut-off means further comprises means for providing a warning signal.

20. A method for measuring the concentration of solid particles in a fluid stream which is susceptible to changes in velocity, said method comprising:

producing a sub-stream of said fluid having a substantially constant and independent velocity;

permitting said sub-stream to come into contact with a triboelectric charging surface, thereby effecting triboelectric charging of said solid particles in said sub-stream; and thereafter measuring the charge produced upon said particles by their impacts on said triboelectric charging surface.

21. A method according to claim 20 further comprising neutralizing pre-existing charges on said particles before said sub-stream contacts said triboelectric charging surface.

22. A method according to claim 20 wherein said sub-stream of fluid is produced by means of a critical flow orifice located in said sub-stream and upstream of said triboelectric charging surface.

* * * * *